(12) United States Patent
Lamare et al.

(10) Patent No.: US 10,275,629 B2
(45) Date of Patent: Apr. 30, 2019

(54) METHOD FOR EXTRACTING MORPHOLOGICAL CHARACTERISTICS FROM A SAMPLE OF BIOLOGICAL MATERIAL

(71) Applicant: SAFRAN IDENTITY & SECURITY, Issy les Moulineaux (FR)

(72) Inventors: François Lamare, Villebon-sur-Yvette (FR); Yaneck Gottesman, Chaville (FR); Bernadette Dorizzi, Paris (FR)

(73) Assignee: IDEMIA IDENTITY & SECURITY, Issy les Moulineaux (FR)

( * ) Notice: Subject to any disclaimer, the term of this patent is extended or adjusted under 35 U.S.C. 154(b) by 117 days.

(21) Appl. No.: 15/272,767

(22) Filed: Sep. 22, 2016

(65) Prior Publication Data

US 2017/0083742 A1 Mar. 23, 2017

(30) Foreign Application Priority Data

Sep. 22, 2015 (FR) .................... 15 58929

(51) Int. Cl.
*G06K 9/00* (2006.01)
*G06T 7/00* (2017.01)
(Continued)

(52) U.S. Cl.
CPC ........ *G06K 9/00013* (2013.01); *A61B 5/0066* (2013.01); *A61B 5/1172* (2013.01); *A61B 5/6826* (2013.01); *G01B 9/02087* (2013.01); *G01B 9/02091* (2013.01); *G06K 9/0012* (2013.01); *G06K 9/00201* (2013.01); *G06T 7/97* (2017.01); *G06K 2209/401* (2013.01); *G06T 2207/10101* (2013.01); *G06T 2207/20221* (2013.01)

(58) Field of Classification Search
CPC ............ G06K 9/00013; G06K 9/0012; G06K 9/00201; G06K 2209/401; G06T 2207/20221; G06T 2207/10101; G06T 7/97; A61B 5/0066; A61B 5/6826; A61B 5/1172; G01B 9/02087; G01B 9/02091
USPC .................................................. 382/124, 125
See application file for complete search history.

(56) References Cited

U.S. PATENT DOCUMENTS

| 9,384,404 B2 * | 7/2016 | Chen ................. G06K 9/00885 |
| 2014/0241596 A1 | 8/2014 | Chen et al. |
| 2015/0168127 A1 * | 6/2015 | Takeno .............. G01B 9/02091 356/479 |

OTHER PUBLICATIONS

Khutlang, Rethabile et al., "Novelty Detection-Based Internal Fingerprint Segmentation in Optical Coherence Tomography Images.", 2014 Second International Symposium on Computing and Networking, pp. 556-559, (2014).

(Continued)

*Primary Examiner* — Sheela C Chawan
(74) *Attorney, Agent, or Firm* — Oliff PLC

(57) ABSTRACT

The present invention relates to a method for extracting morphological characteristics from a sample of biological material, in particular fingerprints, especially internal or external fingerprints, using an optical coherence tomography acquiring system delivering a signal representative of the sample, in which method an image containing intensity data and an image containing phase data are formed from at least the signal delivered by the acquiring system and representative of the sample, in order to extract the morphological characteristics from the sample.

17 Claims, 14 Drawing Sheets

(51) Int. Cl.
G01B 9/02 (2006.01)
A61B 5/1172 (2016.01)
A61B 5/00 (2006.01)

(56) References Cited

OTHER PUBLICATIONS

Darlow, Luke Nicholas et al., "Internal Fingerprint Zone Detection in Optical Coherence Tomography Fingertip Scans.", Journal of Electronic Imaging, vol. 24, No. 2, pp. 023027-1 to 023027-14, (2015).
Liu, Mengyang et al., "Biometric Mapping of Fingertip Eccrine Glands with Optical Coherence Tomography.", IEEE Photonics Technology Letters, vol. 22, No. 22, pp. 1677-1679, (2010).
Bossen, Anke et al., Internal Fingerprint Identification with Optical Coherence Tomography.:, IEEE Photonics Technology Letters, vol. 22, No. 7, pp. 507-509 (2010).
Othman, Nadia et al., "Impact of Quality-Based Fusion Techniques for Video-Based Iris Recognition at a Distance.", IEEE Transactions on Information Forensics and Security, vol. 10, No. 8, pp. 1590-1602, (2015).
May 23, 2016 Search Report issued in French Patent Application No. 1558929.
Fercher, A.F., et al., "Optical Coherence Tomography-Principles and Applications.", Reports on Progress in Physics, No. 66, pp. 239-303, (2003).
Jain, L.C., et al., "Intelligent Biometric Techniques in Fingerprint and Face Recognition.", CRC Press, vol. 10, chapter 2, (1999).
Cappelli, R., et al., "Performance Evaluation of Fingerprint Verification Systems.", IEEE Transactions on Pattern Analysis and Machine Intelligence., vol. 28, No. 1, pp. 3-18 (2006).
Sousedik, C., et al., "Volumetric Fingerprint Data Analysis Using Optical Coherence Tomography.", BIOSIG Conference, pp. 1-6, (2013).
Sousedik, C., et al., "Quality of Fingerprint Scans Captured Using Optical Coherence Tomography.", IJCB Conference, pp. 1-8, (2014).
Hong, L. et al., "Fingerprint Image Enhancement: Algorithm and Performance Evaluation.", IEEE Transactions on Pattern Analysis and Machine Intelligence, vol. 20, No. 8, pp. 1-30, (1998).
Zhou, Jie et al., "A Model-based Method for the Computation of Fingerprints' Orientation Field.", IEEE Transactions on Image Processing, vol. 13, No. 6, pp. 1-16, (2004).
Khalil, M.S., "Deducting Fingerprint Singular Points Using Orientation Field Reliability.", First Conference on Robot, Vision and Signal Processing, pp. 284-286, (2011).
Kimmel, R. et al., Computing Geodesic Paths on Manifolds., Applied Mathematics, vol. 95, pp. 8431-8435, (1998).
Kumar, Ajay et al., "Towards Contactless, Low-Cost and Accurate 3D Fingerprint Identification.", IEEE Conference on Computer Vision and Pattern Recognition, pp. 3438-3443, (2013).
Zigelman, G. et al., "Texture Mapping Using Surface Flattening via Multidimensional Scaling.", IEEE Transactions on Visualization and Computer Graphics, vol. 8, No. 2, pp. 198-207, (2002).

* cited by examiner

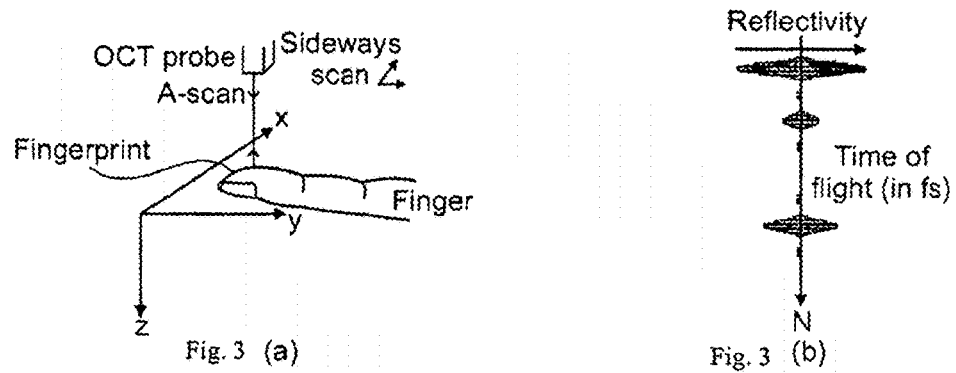
Fig. 3 (a)
Fig. 3 (b)
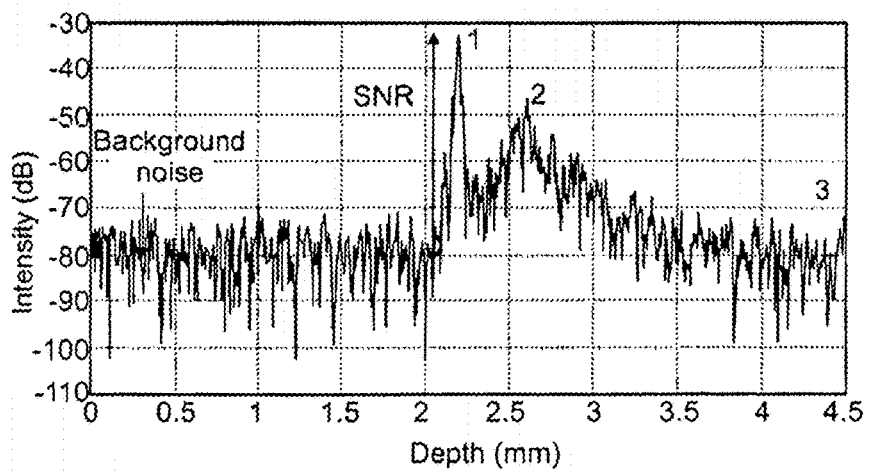
Fig. 4

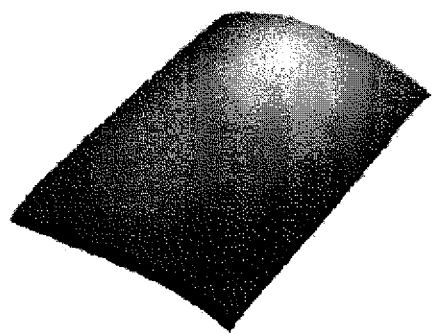
Fig. 13(a)           Fig. 13(b)
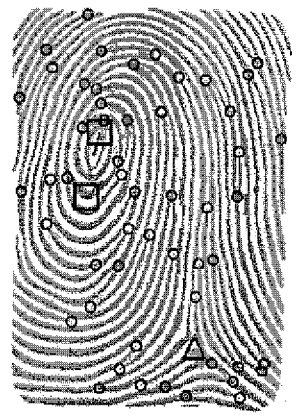
Fig. 14(a)           Fig. 14 (b)

METHOD FOR EXTRACTING MORPHOLOGICAL CHARACTERISTICS FROM A SAMPLE OF BIOLOGICAL MATERIAL

BACKGROUND

The present invention relates to a method for extracting morphological characteristics of biological materials, in particular fingerprints and especially internal or external fingerprints, using signals delivered by optical coherence tomography acquiring devices, especially for biometry.

The optical coherence tomography (OCT) imaging technique is a contactless optical imaging technique that is currently commonly used in the medical sector. It is starting to be used in mass-market applications and especially in biometric applications. At the present time, the problems specific to this type of application are different and intimately related to the study of the properties of surfaces defined from raw three-dimensional data.

By design, an SW-OCT imaging device is an interferential device based on a (Michelson or Mach-Zender) interferometer and a tunable source. Each measurement consists in recording the interferometric signal as a function of the frequency of the source. Complex signals (intensity and phase) are therefore recorded raw in the spectral domain.

These signals are usually represented in the spectral domain (or temporal domain since position may be equated to a time of flight of the light) after Fourier transform of the recorded signal. The complex signal thus obtained is called an A-scan.

For a static object (i.e. an immobile object not subjected to temporal deformation), the spatial phase varies linearly with distance along the z-axis in the vicinity of each achromatic (or reflective) scattering centre.

When the object possesses dynamic properties (deformation and/or movement), any variation in the spatial phase at different measuring times is associated with a Doppler shift.

The spectral phase associated with a scattering centre varies linearly with the frequency $\upsilon$ of the source. The slope of the phase in the spectral domain, which slope is defined by $d\phi_m/d\upsilon$, is proportional to the spatial position of the scattering centre (or to the time of flight taken by the light to reach the scattering centre).

PRIOR ART

In the study of the morphology of the various layers of biological materials located under the skin, as shown in FIG. 1, known methods only exploit intensity data, especially to segment images by intensity in order to map the surfaces separating two separate biological materials. This segmentation is tricky, the intensity of the signal delivered by the OCT sensor being intimately dependent on the tissues located above the tissue of interest. This creates a variability in the segmentation of the images used, which adversely affects the extraction of the sought-after surface. In the field of biometry, images of the internal fingerprint located under the skin, at the "epidermal/dermal" interface obtained after segmentation, contain unexploitable zones with this type of capture and therefore do not always allow an individual to be easily and reliably identified. However, internal prints are better preserved than external prints since they are not subject to the same impairments to their surface properties as the latter i.e. impairments such as scars; marks, for example due to ink or dirt; or even variation in the dampness of the surface of the finger, in particular due to sweat or to ambient humidity conditions. The internal fingerprint is therefore a very relevant biometric datum because it is more stable over time and less dependent on environmental variations. It may moreover allow an individual with a damaged external fingerprint to be authenticated.

The internal fingerprint may also allow an attempt at identity fraud to be detected. Specifically, one known defrauding method, which is difficult to detect with known biometric sensors, consists in depositing, on the finger of the defrauder, an overlayer on which a fingerprint of another person is inscribed in relief. This overlayer is difficult to detect, especially because a real finger with oxygenated blood is located thereunder and the temperature of the overlayer is similar to that of the surface of a real finger.

FIG. 1 shows a typical image obtained from a finger by optical coherence tomography. In this figure, the level of the backscattered signal has been shown as a function of spatial position. As shown in FIG. 3(a), the probe of the OCT sensor has moved, using two galvanometric mirrors, along X and Y axes. For each position of the probe, a measurement obtained by interferometry is recorded, as described in the article by A. F. Fercher et al. *"Optical Coherence Tomography—Principles and Applications"*, published in *"Reports on progress in physics"*, 2003, No. 66, pages 239-303. This consists in a measurement of backscattered intensity as a function of time of flight, i.e. the time that the light takes to pass through the various layers of the examined sample. The propagation distance from the probe may be found by multiplying the time of flight by the speed of light. As shown in FIG. 3 (b), a profile of the reflectivity to light with depth is then obtained, which profile is called an "A-scan".

An exemplary "A-scan" intensity profile of a finger is shown in FIG. 4. The signal of interest corresponding to the signal coming from the external superficial portion of the finger is comprised between the first peak, numbered 1, and the third peak, numbered 3. Before the first peak numbered 1, only background noise is visible. The peak numbered 1 corresponds to the air/skin interface, i.e. to the external fingerprint. It is a question of the interface at which the refractive index difference is the largest, due to the nonuniformity of the two media, inducing the peak with the highest amplitude. In case of attempted fraud, the peak numbered 1 corresponds to the air/overlayer interface. After this peak, the overall intensity of the signal decreases. This decrease is due to the effects of absorption and scattering as the light penetrates into the tissue or the overlayer, and therefore as it penetrates into the various layers of the skin or overlayer.

The detection of the position of the peak of maximum intensity allows the air/skin or air/overlayer interface to be located. By determining the position of the maximum of each "A-scan" profile of the tomographic volume, corresponding to the time of flight of the light between the probe and the external surface of the finger, it is possible to construct a three-dimensional surface, i.e. what is called a 3D surface, associated with the external fingerprint. To selectively form the image of the internal print and to isolate it from the rest of the volume, known methods are based on spatial filtering along the Z-axis. This filtering allows an average level of the backscattered intensity around the depth at which the internal print is located to be obtained. The filtering zone then corresponds to the spatial vicinity of the second main peak of each "A-scan" profile, which peak is directly related to the 3D surface of the internal print. The image thus obtained, called the intensity image, is shown in FIG. 2(a). These methods are especially described in the article by A. Bossen et al. *"Internal Fingerprint identifica-* tion with optical coherence tomography", published in "*IEEE Photonics technology letters*", Vol. 22, No. 7, 2010 and the article by M. Liu et al. "*Biometric mapping of fingertip eccrine glands with optical coherence tomography*" published in "*IEEE photonics technology letters*", Vol. 22, No. 22, 2010. FIG. 2(*b*) shows the image after processing by a matcher software system, the job of which is to convert the image to binary data form and to pinpoint the minutiae of the print i.e. characteristic points of the print used in identification. Certain zones in which the contrast of the print is low appear white. For a given finger, the position of these zones may vary depending on experimental conditions, or on the position of the finger with respect to the sensor. The results obtained from the intensity image may contain zones that are difficult to exploit because of the quality of the images, as may be seen in FIG. 2(*b*).

In the case of the external print, this intensity contrast data furthermore varies greatly depending on the state of the surface of the finger, if it is marked, by ink for example, or moist. Print verification performance is in particular much worse in the case of moist fingers in acquisitions carried out with known sensors, such as for example contact optical or capacitive sensors outputting two-dimensional images, or the contactless optical sensors that are what are referred to as "2½ dimension" sensors, as mentioned in the articles by R. Cappelli et al. "*Performances evaluation of fingerprint verification systems*", IEEE transactions on pattern analysis and matching intelligence, vol. 28, No. 1, 2006, and by L. C. Jain et al. "*Intelligent biometric techniques in fingerprint and face recognition*", chapter 2, Vol. 10, CRC press, 1999. This degradation in performance is also observed with contactless biometric sensors such as OCT sensors. FIG. 5 shows an exemplary experimental cross-sectional OCT image extracted in a conventional way and representing a fingertip with microdroplets on its surface, simulating the behaviour of a finger under sweaty or high-humidity conditions. The intensity image of this exemplary moist finger, which is shown in FIG. 6, contains white spots, due inter alia to the presence of the droplets, which modify the optical properties of the finger locally, creating a parasitic lens effect for example. Known fingerprint readers designed to authenticate individuals thus no longer work under high-humidity conditions, no reliable image of the print of a moist finger being achievable. In the approach presented in the aforementioned article by A. Bossen et al. the acquisition is carried out with the finger making contact with a glass sheet, leading to flattening of the finger.

FIG. 7 shows a cross section in which the papillary dermis, i.e. the internal print, is clearly visible. In the same figure the junction zone, which is located between the dermis and the epidermis, is also shown. The width and position of this zone have been set empirically between 0.1 mm and 0.9 mm in the interior of the finger, in such a way as to contain the interface of the internal print. The complete three-dimensional junction zone may be obtained from the signals $A_{xy}(z)$ of the various A-scans, for a probe position positioned in (x,y). It will then contain the entire 3D internal print. The intensity image I(x,y) of the internal print is then obtained by averaging, along the z direction in the junction zone, the signal $A_{xy}(z)$:

$$I(x, y) = \frac{1}{\Delta_z} \sum_{z \in J} A_{xy}(z)$$

where x and y correspond to the position of the probe, J is the junction zone, and $\Delta_z$ the width of the junction zone. This method allows a 2D image of textures that is what is called an intensity image, denoted I(x,y), and that is related to the average intensity data, to be obtained, x and y being the coordinates of the pixels of the image. Image processing methods have been applied to the image I(x,y) in order to improve its contrast.

In the case where the finger is not flattened during the acquisition, the image I(x,y) may be projected onto the 3D surface of the internal print, which is obtained by virtue of phase measurements. One 3D internal print obtained with this method may be seen in FIG. 8. The performance of this approach in the context of biometry is also not satisfactory because of the degraded quality of the obtained images. US 2014/0241596 and US 2015/016127 disclose methods aiming to represent the flow of blood in the vascular networks of the finger, in order to verify that it is indeed the image of a living finger that is being acquired. The relevant data is here Doppler-type data, and it is proposed to determine differences in phase between successive A-scans (profiles of reflectivity with depth). This treatment necessarily requires the phase in question to be a phase in the "spatial" domain. The phase is not measured in the spectral domain.

The article Novelty Detection-Based Internal Fingerprint Segmentation in Optical Coherence Tomography Images 2014 Second International Symposium on Computing and Networking Rethabile Khutlang et al., discloses a method for segmenting internal prints. The processing is carried out B-scan by B-scan (cross sections) and not A-scan by A-scan (profile of backscattered intensity as a function of depth, or equivalently as a function of time of flight). The print is thus not segmented on the basis of A-scan distance measurements (processing of the signal) but by virtue of clustering methods (GMMs and k-means) applied to the B-scans (image processing). There is no mention of measurements of distances via phase in the spectral domain.

The aim of the article Internal fingerprint zone detection in optical coherence tomography fingertip scans Journal of electronic Imaging 24(2) March/April 2015 is also to segment internal prints. Firstly, the interface of the internal print is crudely segmented using a clustering method. Features allowing the A-scans to be described are chosen for the implementation of the clustering. Secondly, once the internal print has been crudely segmented, the position of the papillary junction (layer of the skin forming the internal print) is more precisely estimated by virtue of image processing operations applied B-scan by B-scan. In this article, the internal print is therefore not segmented on the basis of measurements of distances via phase in the spectral domain. Moreover, no image fusion is carried out.

The article Biometric Mapping of Fingertip Eccrine Glands With Optical Coherence Tomography IEEE Photonics Technology Letters Vol 22, No. 22, Nov. 15, 2010 discloses a method aiming to obtain a map of sweat pores. There is no mention of measurements of distances and more specifically of measurements of distances via phase in the spectral domain.

The article Impact of Quality-Based Fusion Techniques for Video-Based Iris Recognition at a Distance Nadia Othman and Bernadette Dorrizi IEEE TRANSACTIONS on INFORMATION FORENSICS AND SECURITY, VOL 10, No. 8, AUGUST 2015 describes a fusing method implemented to improve the quality of biometric images of the iris originating from a video stream, and not of fingerprints.

SUMMARY

There is a need to improve the quality of data on the external or internal surface morphology of biological materials originating from optical coherence tomography acquiring devices in order, in particular, to effectively extract and identify internal fingerprints and external fingerprints under difficult conditions.

The invention aims to meet this need and it achieves this by virtue of a method for extracting morphological characteristics from a sample of biological material, in particular fingerprints, especially internal or external fingerprints, using an optical coherence tomography acquiring system delivering a signal representative of the sample, in which method an image containing intensity data and an image containing phase data are formed from at least the signal delivered by the acquiring system and representative of the sample, in order to extract the morphological characteristics from the sample.

The image containing intensity data and the image containing phase data are not equivalent in terms of informational content. Even though their qualities are comparable, the data that they contain are complementary, and make it possible to facilitate and optimise the extraction of the morphological characteristics from the sample to be used.

The method according to the invention may thus be used in the field of high-security biometry with the aim of detecting fraud in the identification of individuals, the internal fingerprint in particular being compared with the external print, or with the aim of obtaining a reliable biometric identification under difficult conditions, for example in the case of moist or dirty fingers, or in the case of a relatively faint external fingerprint.

In the case of a moist finger, in the image containing the phase data, the backscattered intensity maxima are always located on the external print, and not on the layer of water or droplets. As the time of flight of the light is known, determining the position of these intensity maxima allows the 3D structure of the external print to be suitably reconstructed. A precise measurement of the time of flight is advantageously obtained from knowledge of the phase of the signal in the spectral domain. The phase image obtained is thus of much higher quality, ensuring a biometric identification performance that is more robust than that obtained from intensity images alone, i.e. images such as obtained by known biometric sensors or indeed with prior-art OCT imaging methods.

Exploiting phase data corresponding to the time of flight of the light makes it possible to compensate for the effect of variability in the scattering intensity of the light on the properties of the image, and especially for the fact that said images are sensitive to the angle of incidence of the lightbeam to the normal of the surface of the sample to be studied.

Phase Image

The second intensity peak of an "A-scan" profile, which peak is numbered 2 in FIG. 4, is attributed to the internal fingerprint, or to the overlayer/finger interface in the case of a fraud. It reflects substantial nonuniformities of the skin in the papillary dermis (a layer of skin located between the dermis and the epidermis) corresponding to a change in cellular organisation, which is visible in FIG. 7. Thus, in the same way as described above, it is advantageous to reconstruct a 3D representation of the internal print by determining the position of the second peak of highest reflectivity in each "A-scan" profile of the tomographic volume.

Once a profile of the reflectivity of the light with depth has been established from the signal representative of the sample, which signal is delivered by the acquiring system, the reflectivity profile containing a plurality of maximum reflectivity peaks, it is possible to determine, in order to form the image containing the phase data, the position of a maximum reflectivity peak of said reflectivity profile, which peak is chosen depending on the type of data to be extracted. The peak of interest for the external print preferably corresponds to the first maximum reflectivity peak of the reflectivity profile, and the peak of interest for the internal print preferably corresponds to the second peak. It is possible to obtain, in the end, 3D surfaces associated with the external or internal prints, depending on the peak in question.

Once the position of the peak of interest has been determined, spatial filtering may be carried out on the signal, in particular passband filtering of the interferogram in the spatial domain, the filtering consisting at least in retaining the interferometric signal contained in a window centred on the peak of interest and of a predefined width that is especially of the order of magnitude of the axial resolution of the OCT acquiring system. A transformation is then advantageously applied to this signal in order to obtain spectral data, especially intensity and phase spectral data, relating to the scattering recorded at the air/finger interface in the case of an external fingerprint or at the epidermal/dermal interface in the case of an internal fingerprint, the transformation especially being a Hilbert transform in order to obtain the complex interferometric signal. To obtain the sought-after phase data, the slope of the phase is advantageously calculated by linear regression of the spectral dependence of the phase, which is obtained from the spectral data obtained by transforming the spatially filtered signal. In the case where the sample is a fingerprint, the reference used to measure the phase data is preferably the average envelope of the surface of the finger. This average envelope corresponds to the surface enveloping the finger without its valleys, as shown in FIG. 9. A 3D surface may be coded as a topographical image $S(x,y)$ in which each $(x,y)$ is associated with a depth value or preferably here a time of flight or phase value. The average envelope, called $Em(x,y)$, is then obtained by applying an averaging filter and especially a 2D passband filter to the topographical image $S(x,y)$. Since the valleys have higher spatial frequencies, the latter are advantageously removed during the filtering operation.

For the internal print, the average envelope corresponds to an internal surface of the finger, which surface is located level with the internal print and obtained by filtering the tomographic image associated with the 3D surface of the internal print.

A 2D image of textures $P(x,y)$, which is what is called a phase image, may be obtained by subtracting $S(x)$ and $Em(x,y)$: $P(x,y)=S(x,y)-Em(x,y)$. In this way, the time-of-flight or phase measurements are no longer taken with reference to the probe of the sensor but with reference to the average envelope. Therefore, the resulting image advantageously shows not the phase values $\Phi$, but rather their variations $\Delta\Phi$, this allowing a texture image of higher contrast to be obtained.

The contrast of this texture image may be further improved by applying an adaptive histogram equalisation then a contrast adjustment using a sigmoid function, the middle of which is determined by the Otsu method, which consists in assuming that the image to be binarised contains only two classes of pixels, namely foreground and background pixels, and in calculating the optimum threshold separating the two classes so that their intra-class variance is minimised.

In the same way as for the image $I(x,y)$, the texture image $P(x,y)$ may be projected onto the 3D surface of the internal print shown in FIG. 11(a).

The invention allows fraud using overlayers to be detected by comparison of the fingerprint associated with the first maximum reflectivity peak and the fingerprint associated with the second peak. If these prints are different, a fraud is being attempted.

Another subject of the invention, according to another of its aspects, is a method for generating an image including a datum related to the position of an interface between two media, especially the air and skin or dermis and epidermis, from an interferogram of an internal or external finger or palm print obtained by SW-OCT in the spectral domain, including the steps consisting in:
- applying a transform, especially a Fourier transform, to the interferogram to generate a reflectogram in the time domain; and
- estimating from this reflectogram a spatial position of the interface corresponding to the image of the internal or external print that it is sought to image.

The spatial position may be estimated from the envelope of the signal of the reflectogram, by taking this position to be the local maximum of the amplitude of the envelope of the signal level with a reflectivity peak corresponding to the sought interface.
- Preferably, the position is determined by applying a passband filter to isolate the reflectivity peak corresponding to the sought interface and by applying to the reflectogram thus filtered an inverse transform, especially an inverse Fourier transform, to generate a filtered interferogram in the spectral domain.
- This interferogram may be used to determine the slope of the linear regression line of the spectral phase $\phi(\upsilon)$ as a function of frequency b, then the time of flight $\tau_0$ and the position $z_0$ of the interface corresponding to the reflectivity peak by the formula $$\tau_0 = 1/2\pi d\phi(\upsilon)/d\upsilon = z_0/c$$

A 3D surface may be generated from knowledge of the position z0, at each point x,y, of the reflectivity peak in question, and therefore of the interface in question. The first peak may give the position of the air/skin interface, corresponding to the external print, and the second that of the epidermis/dermis interface corresponding to the internal interface.

2D passband filtering may be applied to such a surface to obtain an average envelope Em(x,y) of the position of the interface.

This envelope may be taken as a reference to generate by subtraction a phase texture image P(x,y).

This phase texture image may be fused with an intensity texture image I(x,y) to obtain a fused texture image, which may then be projected onto a 3D surface in order to obtain a flattened 3D textured print surface.

It is possible in this way to obtain images of internal and external fingerprints.

Fusion of the Intensity and Phase Images

In one preferred embodiment of the invention, the image containing intensity data and the image containing phase data are fused to form a single image.

To do this, the structure of each image containing intensity data and phase data, respectively, is analysed in order to establish, for each image, a confidence map containing, for each pixel, a quality value depending on the neighbouring pixels. The confidence maps of the images are especially based on an assessment of contrast and on the local quality of the valleys present in the images, in the case of a fingerprint.

Each pixel of the image F fused from the image I containing intensity data and the image P containing phase data is advantageously generated by a linear combination of the values of the corresponding pixels of the two images, said values being weighted by the quality values of the confidence maps, i.e.:

$$F(x,y) = \alpha_I(x,y) \times I(x,y) + \alpha_P(x,y) \times P(x,y),$$

where for example $$\alpha_I = \frac{C_I(x, y)}{Norm}; \alpha_P = \frac{C_P(x, y)}{Norm};$$

(x, y) are the coordinates of a pixel; $C_I(x, y)$ is the quality value of the pixel (x, y) of the image I, $0 < C_I(x, y) < 1$; $C_P(x, y)$ is the quality value of the pixel (x, y) of the image P, $0 < C_P(x,y) < 1$; and Norm=$C_I(x, y) + C_P(x,y)$. If Norm=0, preferably $\alpha_I = \alpha_P = 0.5$. Depending on the fusion formula used, the values $\alpha_I$ and $\alpha_P$ may be expressed differently; the invention is not limited to a particular calculation for the values $\alpha_I$ and $\alpha_P$.

In one variant, the image fused from the image containing intensity data and the image containing phase data is advantageously formed by retaining, for each pixel, the pixel of the image having the highest quality value:

$$F(x, y) = \begin{cases} I(x, y) & \text{if } C_I(x, y) > C_P(x, y) \\ P(x, y) & \text{if } C_I(x, y) < C_P(x, y) \end{cases}.$$

The image fused from the image containing intensity data and the image containing phase data is thus advantageously formed pixel by pixel, depending on the neighbours of each pixel, by virtue of the confidence maps.

In the case where the image in question is a fingerprint, the quality value of a pixel, ($C_P(x, y)$ or $C_I(x, y)$), may be obtained from print valley orientation field reliability maps, as described in the articles by J. Zhou and J. Gu, *"A Model-based for the computation of fingerprint's orientation field"*, IEEE Transactions on Image Processing, vol. 13, no. 6, 2004, and by M. S. Khalil, *"Deducting fingerprint singular points using orientation field reliability"*, First conference on robot, vision and signal processing, pp. 234-286, 2011. The orientation fields of the valleys represent the direction of the valleys at each position on the print. They are calculated for each pixel of the fingerprint image, depending on the neighbours thereof. It is known to use such orientation fields in fingerprint biometry, for example in methods for improving fingerprint images such as that described in the article by L. Hong et al. *"Fingerprint image enhancement: algorithm and performance evaluation"*, IEEE Transactions on Pattern Analysis and Machine Intelligence, vol. 20, no. 8, 1998. These orientation field reliability maps allow the validity and reliability of the estimation of the orientation of the valleys to be evaluated.

A low-quality fingerprint image region may be characterised by the fact that the texture of the valleys is not apparent, the periodic structure that is characteristic of the valleys being absent. In such regions, the estimation of the orientation is poor because there is no preponderant orientation. Therefore, the value of the reliability is low. In contrast, in highly structured print regions, the presence of a particular direction may be estimated reliably. The value of the reliability for these regions is high.

As explained in the articles by C. Sousedik et al. *"Volumetric Fingerprint Data Analysis using Optical Coherence Tomography"*, BIOSIG Conference, 2013, pp. 1-6, and by C. Sousedik and C. Bush, *"Quality of fingerprint scans captured using Optical Coherence Tomography"*, IJCB Conference, 2014, pp. 1-8, the structure of the internal print may be quite nonuniform, contrary to that of the external print, which is fairly continuous, this leading to ambiguity in the position of the second maximum reflectivity peak. The structure of the internal print may also vary greatly from one individual to the next. Detecting the position of the internal print via time-of-flight measurements may be tricky, insofar as the interface is not necessarily well defined.

Furthermore, the backscattering of light in the skin involves complex physical effects that are difficult to model, these effects being associated with interference between the multiple waves backscattered by the biological structures of the skin. It is not obvious that, in a fingerprint, the tops of the valleys correspond to reflectivity maxima and the bottoms to minima, or vice versa.

Fusing the phase and intensity images makes it possible to better take advantage of the data available in both the two images, and thus to substantially improve the quality of the obtained final image of the sought-after surface. For example, in the biometric sector, a substantial improvement in the performance of identification based on the subcutaneous print is obtained using known biometric identification algorithms.

Location Precision

The precision with which the maximum reflectivity peaks may be located in part determines the quality of the 3D and 2D phase images. This location precision, which is different from axial resolution, is a notion that is neither well known in the prior art nor frequently used in biomedical applications.

Axial resolution corresponds to the minimum distance required between two scattering centres for them to be correctly distinguishable, and it is only dependent on the spectral width of the light source. It may be measured from the full-width at half maximum of a peak associated with a single scattering centre, for example the first peak numbered 1.

Location precision is advantageously related to the error in the location of the maxima of the envelope of the various "A-scan" profiles. In order to evaluate location precision, a statistical study is carried out, consisting in simulating the peak associated with a single scattering centre, the position of which is set in the simulation, the simulation also taking into account the various noise contributions of the photodetector of the acquiring system, these contributions mainly being due to thermal noise and shot noise, which have distributions that may be likened to a white noise. Depending on its power, this noise may have a relatively substantial impact on the measured position of the peak maximum. The error in the position may be evaluated by determining the difference between the position of the maximum of the noisy simulated "A-scan" profile and that of the reference "A-scan" profile used, which is known beforehand. Thus the location precision of the acquiring system is defined by the standard deviation of this location error. This standard deviation is advantageously obtained from a large number of random draws of noisy "A-scan" profiles.

Device

According to another of its aspects, the invention relates to a device for extracting morphological characteristics from a sample of biological material, in particular fingerprints, especially internal or external fingerprints, comprising an optical coherence tomography acquiring system delivering a signal representative of the sample, the device being configured to form, from at least the signal delivered by the acquiring system and representative of the sample, an image containing intensity data and an image containing phase data, in order to extract the morphological characteristics from the sample.

In one preferred embodiment of the invention, the device is furthermore configured to fuse the image containing intensity data and the image containing phase data in order to form a single image.

The features described above with regard to the method according to the invention apply to the device.

The field of view of the device, corresponding to the maximum spatial extent in the XY plane able to be recorded, may be large, for example as much as 2 mm by 2 mm, namely 4 $mm^2$, and better still 2 cm by 2 cm, namely 4 $cm^2$. This allows a substantial number of minutiae to be obtained in the case of extraction of a fingerprint.

BRIEF DESCRIPTION OF THE DRAWINGS

The invention will possibly be better understood on reading the following detailed description of nonlimiting examples of implementation thereof, and on examining the appended drawings, in which:

FIGS. 3(a) and 3(b), which were described above, respectively show the acquisition of a fingerprint by tomography and the obtained "A-scan" profile, as a function of the time of flight of the light;

FIG. 4, described above, shows the intensity of an "A-scan" profile as a function of depth;

FIGS. 13(a) and 13(b) illustrate a comparison between two phase images obtained according to the invention;

FIGS. 14(a) and 14(b) show, respectively, the image fused from the phase and intensity data and the processed image both obtained according to the invention;

DESCRIPTION OF EXEMPLARY EMBODIMENTS

Figure 10:
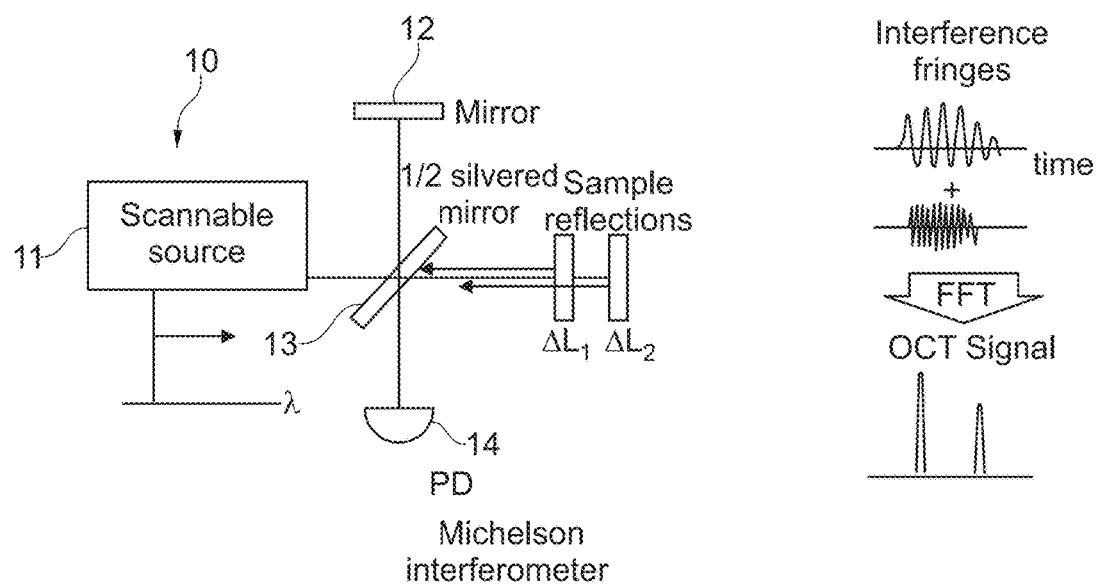
FIG. 10 shows an OCT device according to the invention.

An OCT device 10 allowing the invention to be implemented is shown in FIG. 10. This device 10 includes a scannable source 11 configured to scan the sample at various depths, a mirror 12, a half-silvered mirror 13 and a Michelson interferometer 14. Each wavelength scan or "A-scan" produces interference fringes from reflections from the sample at various depths.

An exemplary method according to the invention will now be described with reference to FIGS. 23 to 25 for each x,y position of the probe.

Figure 23:
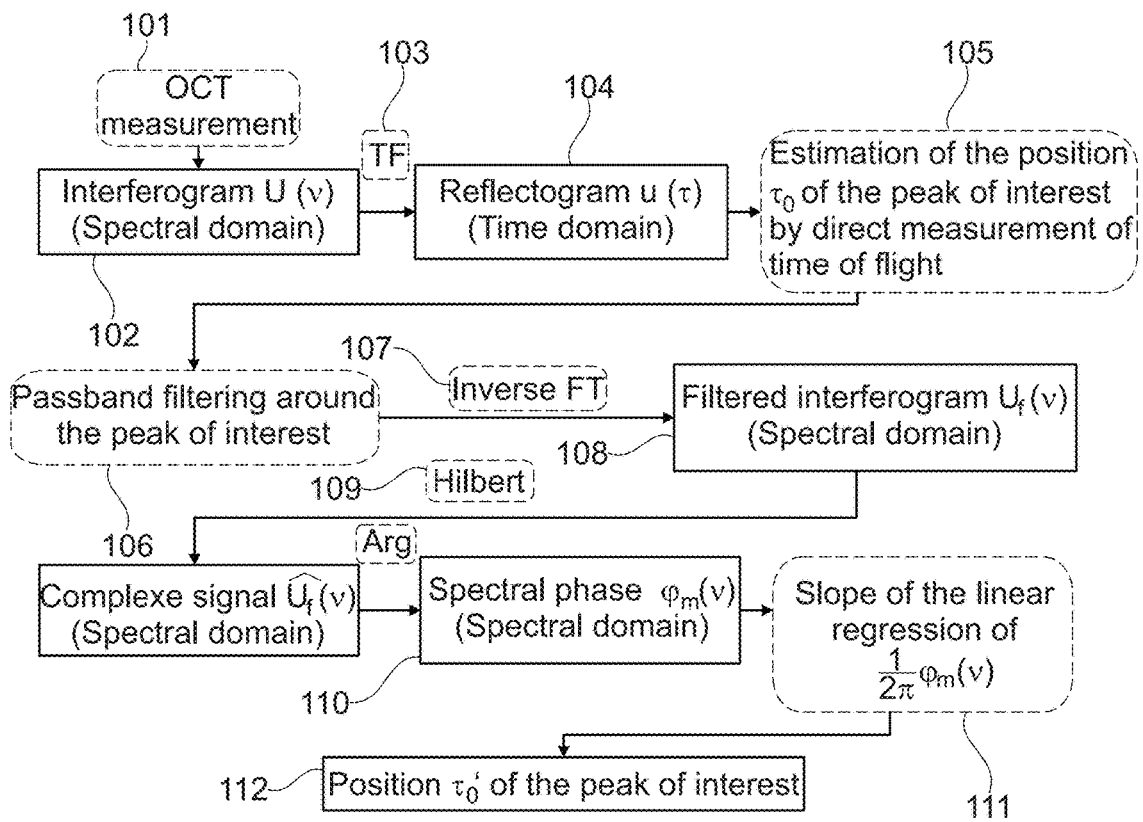
FIGS. 23 to 26 illustrate various steps of an exemplary method according to the invention.

As illustrated in FIG. 23, to obtain the phase images P(x,y) it is possible to begin with a spectral-domain interferogram 102 obtained from an SW-OCT measurement (step 101).

By Fourier transform 103 a time-domain reflectogram 104 is obtained, which allows (step 105) the position of the peak of interest (air/finger interface, epidermis/dermis interface, etc.) to be estimated by direct measurement of the time of flight, using the envelope of each A-scan.

This reflectogram 104 may be subjected to passband filtering in the spatial domain about the peak of interest (step 106), this isolating this peak, and then a filtered interferogram may be obtained in the spectral domain by inverse Fourier transform 107.

A Hilbert transform 109 may allow a complex signal to be obtained in the spectral domain, the argument of which gives the spectral phase 110, and a statistical treatment 111 by linear regression may allow the slope $d\phi(\upsilon)/d\upsilon$ of the gradient, and therefore the time of flight 102 of the peak of interest, i.e. its spatial position, to be obtained.

The image generated from the spectral phase data consists, in this example, in a grey-level representation of the time of flight t(x,y). In this representation, the spatial resolution of the measurement is not degraded. The variation in the time of flight along the x and y axes allows the morphological characteristics of the print to be accessed.

Such an image differs from the intensity image in mode proposed in the article by Bossen et al. cited above. Specifically, rather than imaging the time of flight t(x,y), Bossen proposes to image I(x,y), where I(x,y) is the average intensity of the envelope of the A-scan in the vicinity of the peak of interest. The zone of spatial averaging considered, which is typically between 100 µm-900 µm in size, is much larger than the spatial resolution of the instrument. In this representation, it is the variation in the intensity I along the axes x and y that allows the morphological characteristics of the print to be accessed.

Figure 24:
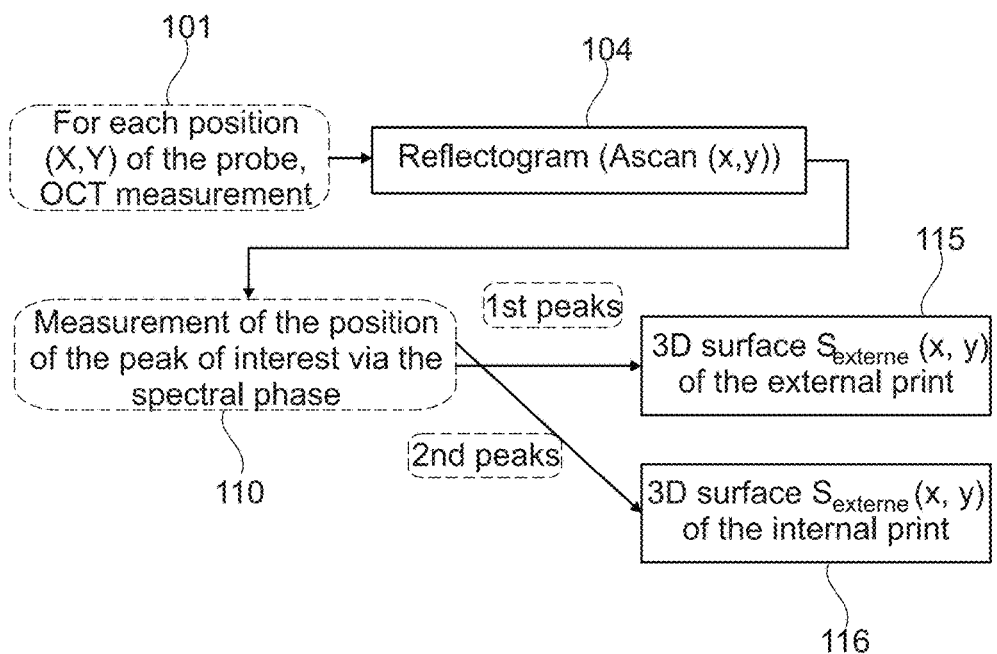

FIG. 24 illustrates, for each x,y measurement 101 and associated A-scan reflectogram 104, that it is possible to apply the method described with reference to FIG. 23 to precisely measure the position 110 of the peak of interest via knowledge of the spectral phase $\phi(\upsilon)$, in order to obtain 3D surface images of the external print 115 and of the internal print 116.

Figure 25:
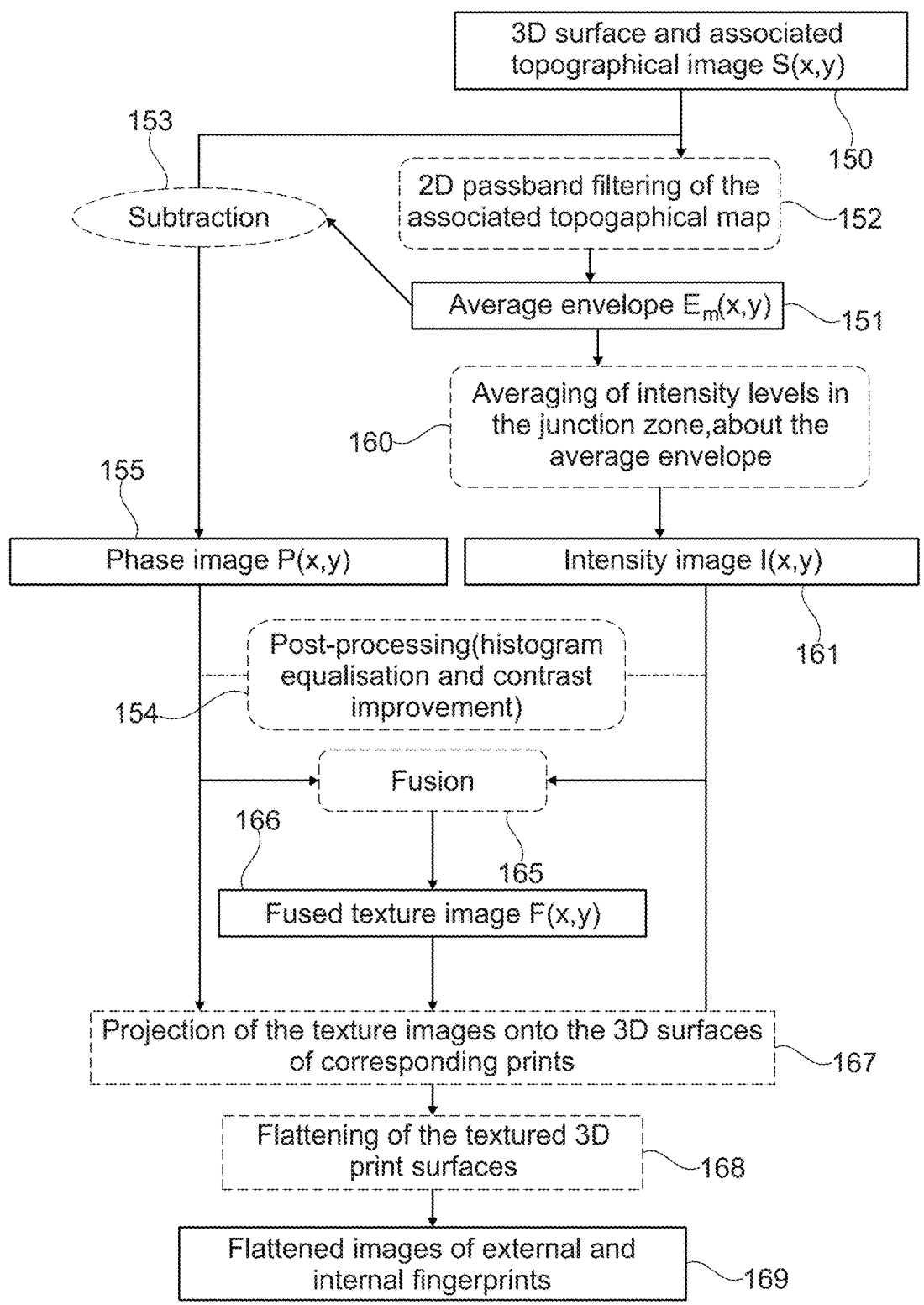

With reference to FIG. 25, an exemplary method for fusing phase and intensity images, after the 3D surfaces of the prints have been extracted by a process 140 such as for example described with reference to FIGS. 23 and 24, will now be described.

In the case where the sample is a fingerprint, the reference used to measure the phase data is preferably the average envelope of the surface of the finger. This average envelope corresponds to the surface envelope of the finger without its valleys. A 3D surface may be coded as a topographical image S(x,y) 150 in which each (x,y) is associated with a time of flight or phase value. The average envelope 151, called Em(x,y), is then obtained by applying an averaging filter 152 and especially a 2D passband filter to the topographical image S(x,y). Since the valleys have higher spatial frequencies, the latter are removed during the filtering operation.

A 2D image of textures P(x,y), which is what is called a phase image, may be obtained by subtracting (step 153) S(x) and Em(x, y): P(x,y)=S(x,y)−Em(x,y). In this way, the time-of-flight or phase measurements are no longer taken with reference to the probe of the sensor but with reference to the average envelope. Therefore, the resulting image 155 advantageously shows not the spectral phase values $\Phi_m$, but rather their variations $\Delta\Phi$, this allowing a texture image of higher contrast to be obtained.

Figure 26:
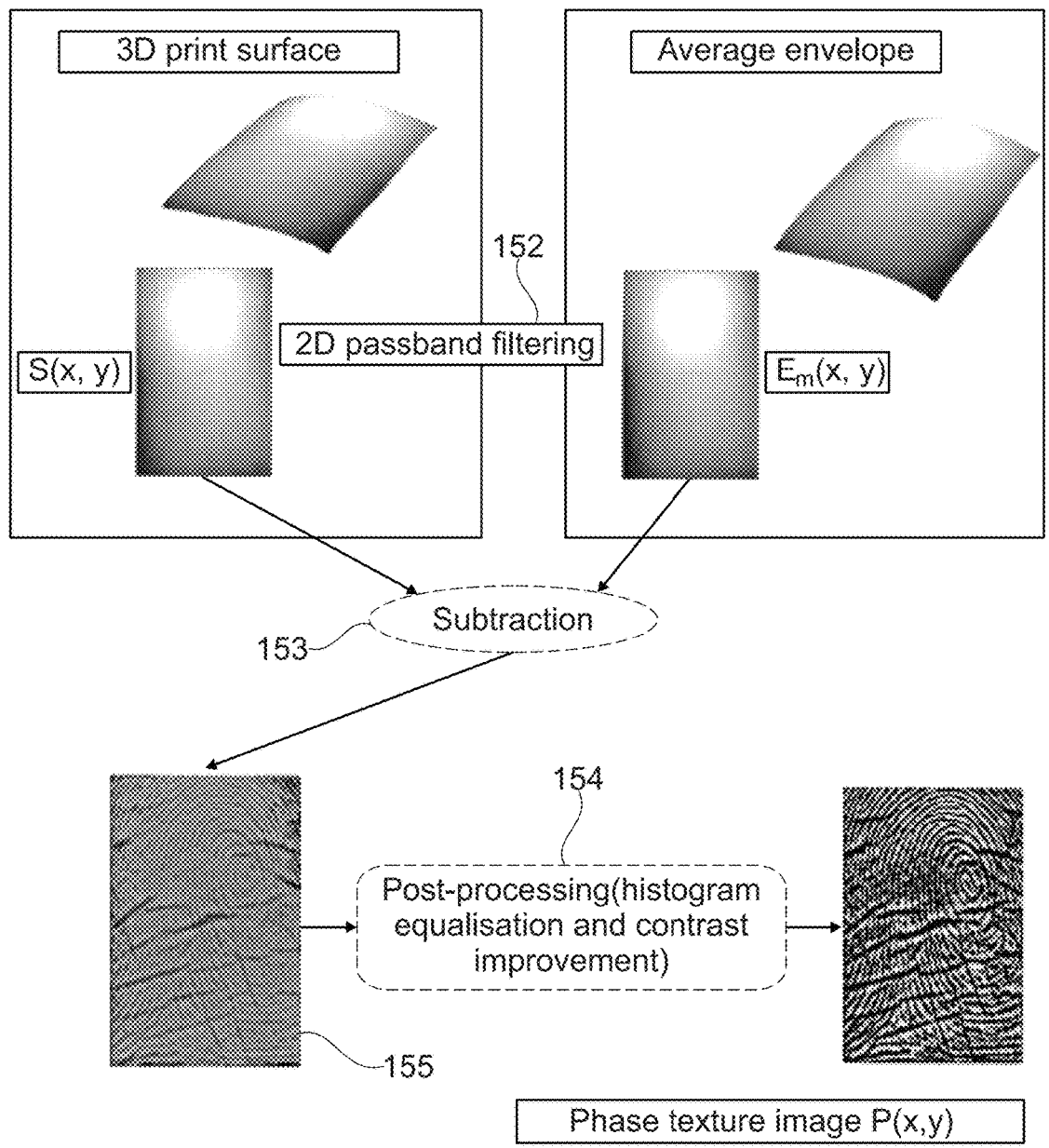

FIG. 26 illustrates an exemplary result obtained by performing these operations. The contrast of this texture image may be further improved by applying an adaptive histogram equalisation (step 154) then a contrast adjustment using a sigmoid function, the middle of which is determined by the Otsu method, which consists in assuming that the image to be binarised contains only two classes of pixels, namely foreground and background pixels, and in calculating the optimum threshold separating the two classes so that their intra-class variance is minimised.

Knowledge of the average envelope also allows the intensity levels to be averaged (step 160) to obtain an intensity texture image 161, which may also undergo contrast-adjusting processing (step 154).

The phase image P(x,y) and intensity image I(x,y) may be fused in step 165 to obtain a fused texture image 166. These texture images may be projected (step 167) onto the corresponding 3D surfaces.

The 3D surfaces thus textured may be flattened (step 168) to obtain flattened internal and external print images 169.

Figure 1:
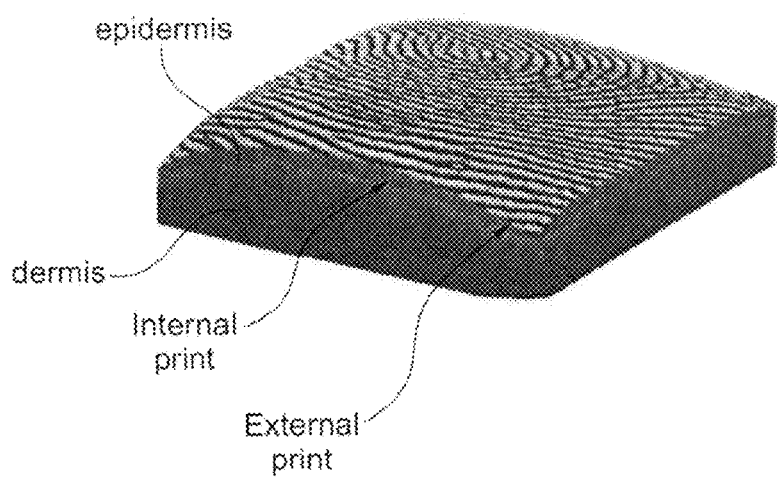
FIG. 1, described above, shows a volumetric image obtained, with an optical coherence tomography acquiring system, from a finger.
Figure 11:
FIG. 11(a) shows the phase image and FIG. 11(b) shows the intensity image of the internal print, which images are projected onto the corresponding 3D surface, these images being obtained by implementing the method according to the invention on the tomographic volume in FIG. 1.
Figure 11:

A 3D phase image of an internal print, which image was obtained according to the invention from the tomographic volume in FIG. 1, is shown in FIG. 11(*a*).

The intensity image of the same internal print, which image is shown in FIG. 11(b), contains unusable zones of very low contrast. These zones are random because they depend inter alia on the local scattering properties of the biological tissue but also on the angle of incidence of the probe of the optical coherence tomography acquiring system, especially in the case of a contactless measurement where the measurement is not reproducible.

Figure 2:
FIGS. 2(a) and 2(b), which were described above, respectively show the intensity image and the processed image obtained, according to the prior art, from the volume in FIG. 1.
Figure 2:
Figure 5:
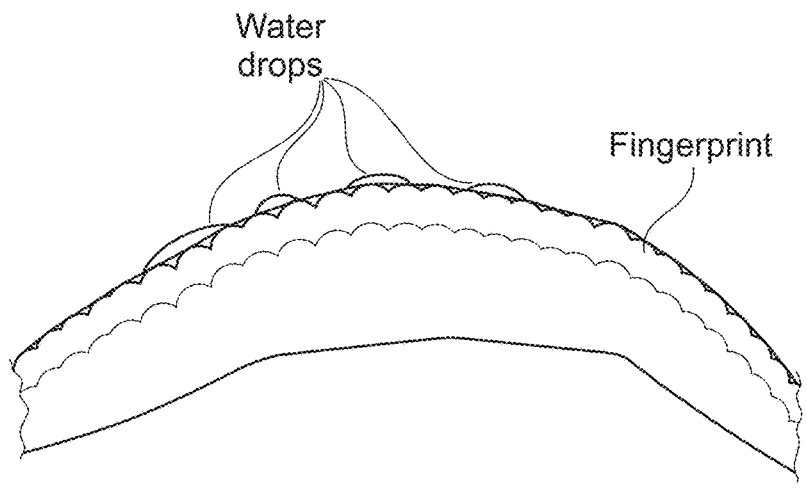
FIG. 5, described above, illustrates the presence of water droplets on the surface of a finger.
Figure 6:
FIG. 6, described above, shows the intensity image of the moist finger in FIG. 5, the image being obtained by OCT according to the prior art.
Figure 7:
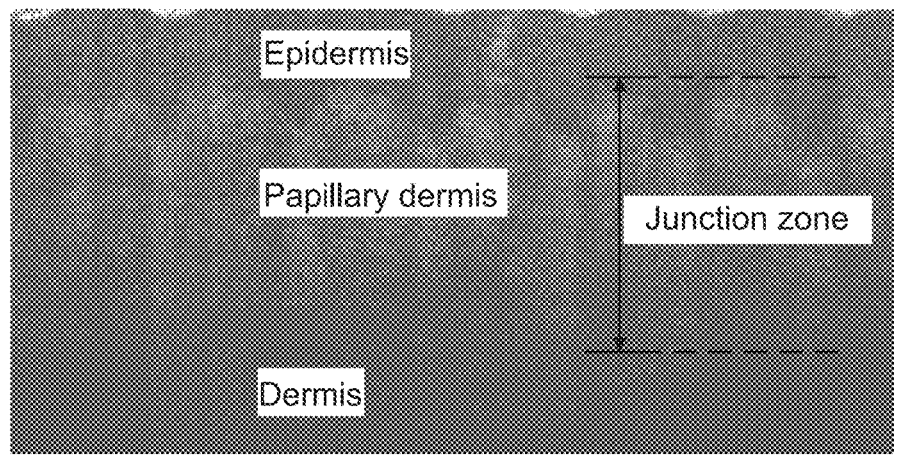
FIG. 7, described above, shows a cross section through a tomographic volume obtained according to the prior art.
Figure 8:
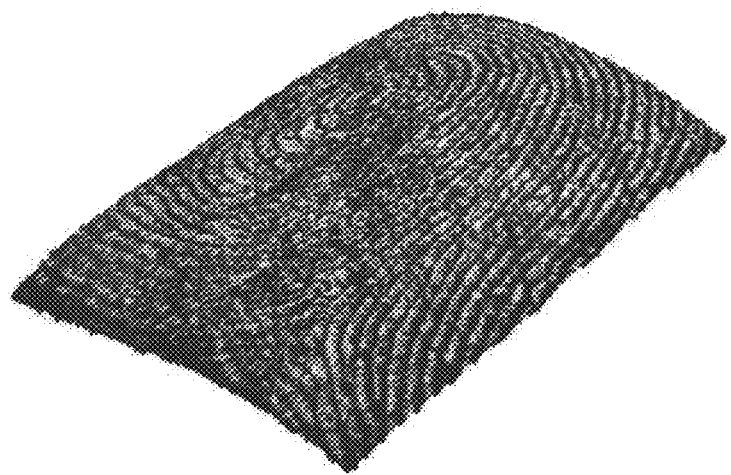
FIG. 8, described above, shows the 3D internal fingerprint obtained from the volume in FIG. 7, said fingerprint being obtained according to a prior-art method.
Figure 9:
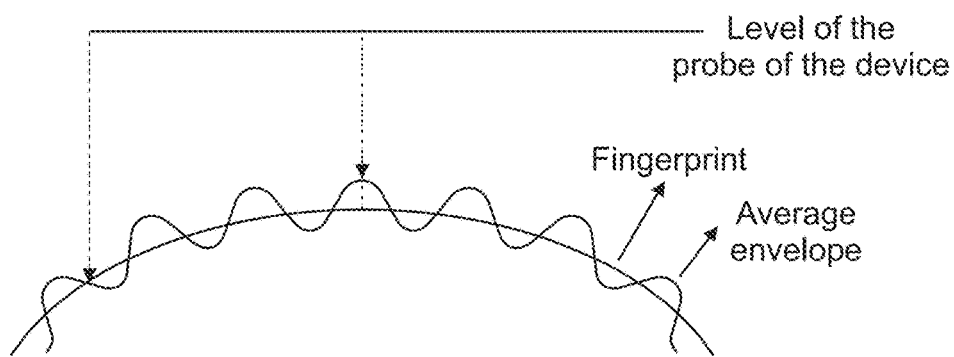
FIG. 9, described above, illustrates the average envelope of the surface of a finger.
Figure 12:
FIGS. 12(a) and 12(b) respectively show the phase image and the processed image of the internal print, which images were obtained, according to the invention, from the tomographic volume in FIG. 1.
Figure 12:
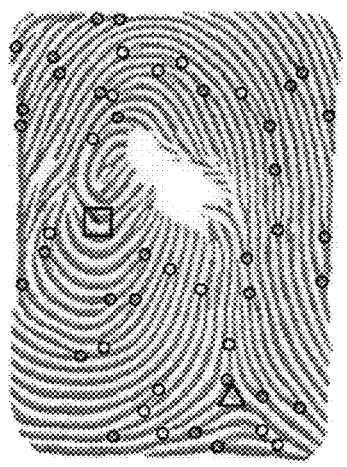

FIG. 12(a) shows a raw phase image, FIG. 12(b) showing the corresponding image delivered as output from a matcher. These images are to be compared to the intensity images shown in FIG. 2, which was described above. The positions of the unusable zones of the image in FIG. 12(b) are different from those in FIG. 2(b). Thus, using both the characteristics extracted from the intensity image and those extracted from the phase image allows the identification of the the individual corresponding to this fingerprint to be improved.

FIG. 13(a) shows a 3D image of the external print, onto which phase data has been projected, which data was obtained from the tomographic volume in FIG. 1, according to the invention. The high values, shown in white, correspond to a short time of flight between the probe of the OCT acquiring system and the surface of the print, and low intensity values, shown in black, correspond to a longer time of flight. This example does not allow good quality print images to be obtained directly, insofar as it is not possible to suitably discern the valleys. This is due to the fact that the reference for the time-of-flight measurement, i.e. the probe of the OCT acquiring system, is not located at an equal distance from all the points on the surface of the finger. In order to obtain a better contrast, as described above, the average envelope of the surface of the finger is taken as reference for the time of flight. As may be seen in FIG. 13(b), showing a 3D print onto which delta-phase data, i.e. phase variations, have been projected (these variations being the relevant data for obtaining well contrasted print images), the valleys are clearly visible in this case.

As described above, the image containing intensity data and the image containing phase data are fused to form a single image, using confidence maps of each image, these maps providing quality values pixel by pixel. An image formed by fusing the intensity image in FIG. 2(a) and the phase image in FIG. 12(a) is shown in FIG. 14(a), the corresponding image as output from a matcher being shown in FIG. 14(b). By virtue of the fusion, the resulting image is of much higher quality, unusable zones having almost disappeared.

Figure 15:
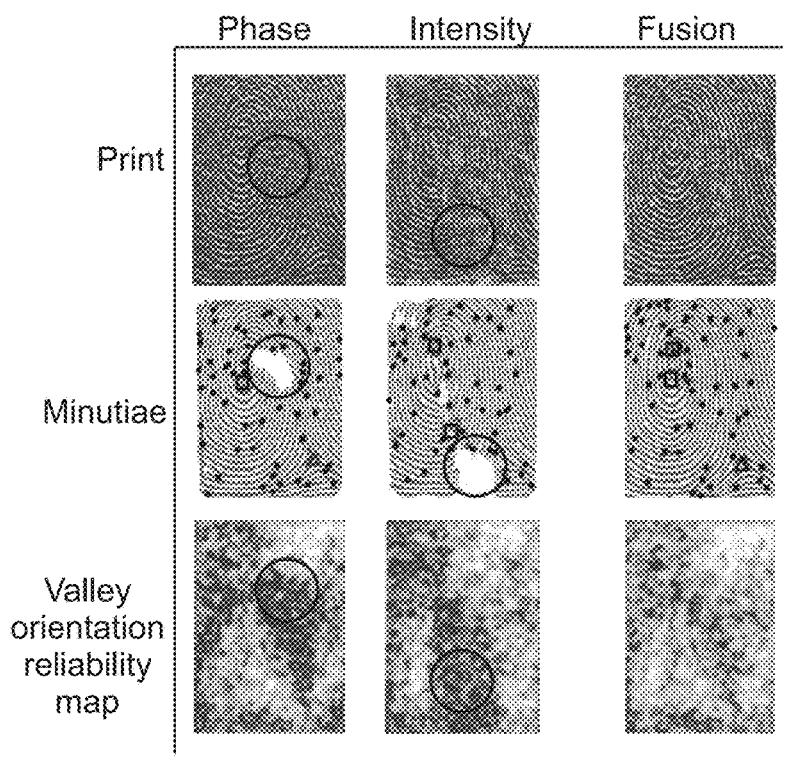
FIG. 15 shows internal fingerprints, the associated minutiae, and the valley orientation reliability map for the phase and intensity images and for the image fused therefrom, obtained according to the invention.

FIG. 15 shows internal fingerprints, the associated minutiae, and the valley orientation reliability map for the phase and intensity images and for the image fused therefrom. Complemented images have been shown as this is the conventional fingerprint format. The images in the first row correspond to flattened internal print images, in the three representations. The images in the second row show the same images after pre-processing and binarising steps, the software package Verifinger, which was developed by Neurotechnology, having been used in the described example. In these images, the minutiae extracted from the binary image, which minutiae are represented by black dots and exploited by matchers, are used in the identifying step, the minutiae of the two fingerprint images being matched. In the two, phase and intensity, representations, the image quality is mediocre in certain regions, as shown by the black circles. In such regions, the valleys of the fingerprints are not visible. Therefore, the quality of these regions is not high enough to ensure correct detection of the minutiae, as illustrated by the white holes in the binarised images. In the representations of the valley orientation field reliability maps, dark pixels correspond to low reliability values whereas light pixels correspond to high values. In the intensity and phase representations, low reliability values are associated with zones of poor quality. It will be noted that, preferably and in the described example, the problematic regions are not located in the same location in the two representations.

As may be seen in the last column in FIG. 15, the internal fingerprint image obtained after the intensity and phase images have been fused is of much higher quality, this image having been reconstructed by choosing the best regions of the two representations. The structure of the valleys is better preserved throughout the image. The regions containing holes have disappeared from the binarised image, this leading to a more robust detection of minutiae. The reliability map for the image after fusion clearly illustrates the improvement in the overall quality of the image, light zones being more numerous and more extensive.

Figure 16:
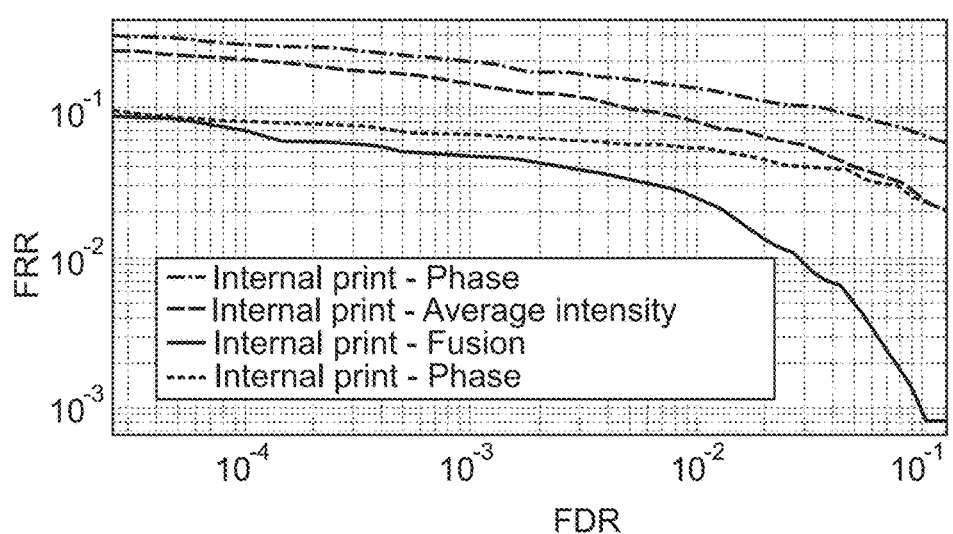
FIG. 16 is a graph showing performance curves obtained by implementing the method according to the invention.

FIG. 16 shows a comparison of the performance obtained with results originating from various representations for a database comprising about one hundred fingers, in terms of false detection rate FDR as a function of false rejection rate FRR. These detection error trade-off (DET) curves giving the false detection rate as a function of false rejection rate are a known way of evaluating the performance of biometric systems. The lower these curves, the better the performance, a minimum false rejection rate being sought for a given false detection rate. The dotted curve corresponds to a reference curve, which was obtained with a phase image of the external print, this print being by nature easily accessible to different sensors.

The dashed curve and the dash-dotted curve correspond to the curves for internal prints extracted from intensity and phase images, respectively, and are at about the same level. For a false detection rate of $10^{-3}$ for example, the false rejection rate is degraded by a factor of 2-3 with respect to the false rejection rate associated with the reference curve. This result bears witness to how difficult it is to access the internal print. The continuous curve was calculated from images after fusion. For a given false detection rate, the false rejection rate is decreased by a factor of about 3-4 relative to that associated with the curves corresponding to phase and intensity images of internal prints. To give another example, for a false detection rate of 0.01%, the false rejection rate is about 7% for images after fusion, compared to 26% for phase images and 20% for intensity images. For a false detection rate of 0.1%, the false rejection rate is about 4% for images after fusion, compared to 20% for phase images and 14% for intensity images. It will furthermore be noted that a better performance is obtained with internal print images after fusion than with phase images of external prints, internal prints being better preserved than external prints.

Figure 17:
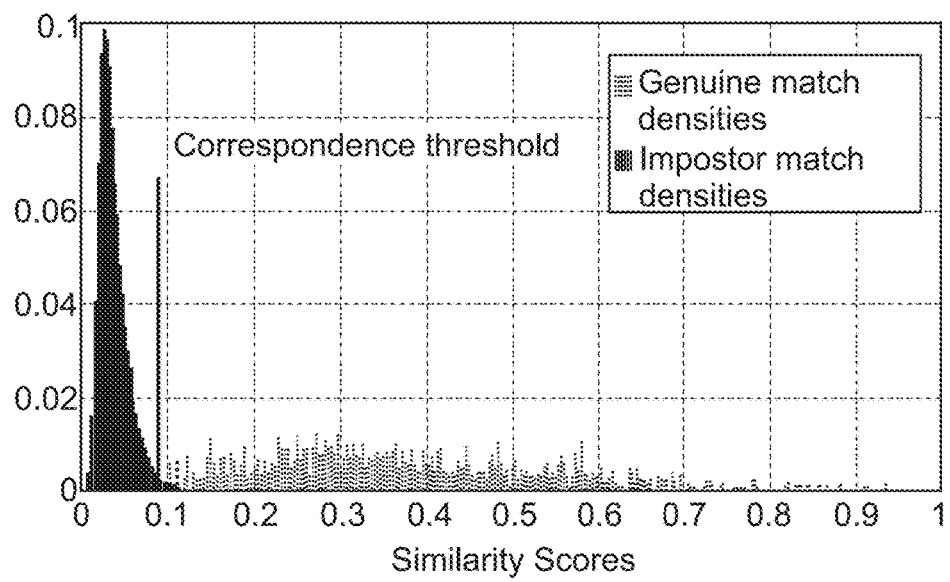
FIG. 17 is a graph showing the probability densities of genuine-matching scores and impostor-matching scores, using a database of images of internal prints extracted according to the invention.

FIG. 17 shows the probability densities of the impostor-matching and genuine-matching scores obtained with a database of internal print images extracted according to the invention, the database containing 102 different fingers obtained from 15 individuals, each finger having been acquired 4 times. The internal print images in the three, intensity, phase and post-fusion, representations were extracted from tomographic volumes. For the verification tests, each internal print image was compared with all the other images of the database, leading to a total of 166056 print comparisons. The comparison of two images originating from a given finger is called genuine matching and the comparison of two images originating from different fingers is called impostor matching. The similarity scores are calculated with the software package NBIS (NIST Biometric Image Software). In this example, the algorithm MINDTCT allows the minutiae of a print image to be extracted and the matcher BOZORTH3 returns the similarity score of two images. Two score probability densities, the genuine-matching density and the impostor-matching density, are obtained, the discernability of these densities allowing the performance of a biometric system to be quantified. The final decision is taken by comparing the similarity score obtained to a threshold, which is chosen depending on the score densities and the desired performance. As the genuine-matching and impostor-matching densities overlap, false rejection errors or false detection errors are made during the decision-making process. The verification performance is lastly evaluated using performance curves obtained by varying the correspondence threshold.

Figure 21:
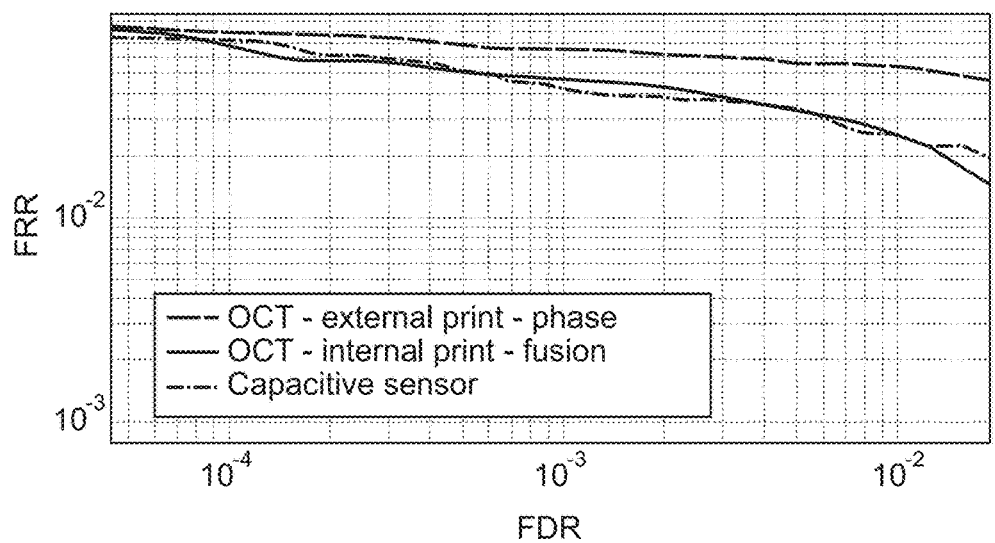
FIG. 21 is a graph showing comparative performance curves.

The results obtained demonstrate that the internal print allows individuals to be identified with a performance comparable to that obtained when known biometric readers are used to read the external print of a dry finger. Individuals with dirty or moist fingers are also identified more effectively than is possible using known biometric systems. FIG. 21 shows a comparison of the performance obtained using internal prints extracted by fusion according to the invention with the performance obtained using external prints extracted by a sensor according to the prior art, a capacitive 2D sensor in the example. A similar FRR is obtained for a given FDR.

By extension, in the case of moist fingers, the performance obtained using internal prints extracted by fusion according to the invention is better than the performance obtained with sensors according to the prior art, a capacitive 2D sensor for example. Specifically, the performance of capacitive 2D sensors in the moist case is necessarily worse than that presented for the normal case, as illustrated by the dashed curve in FIG. 21.

Figure 18:
FIG. 18 shows an intensity image of a fingerprint in the case of a moistened finger.
Figure 19:
FIGS. 19(*b*) and 19(*a*) show, respectively, an image of a fingerprint in the case of the moistened finger in FIG. 17 after fusion, this image being obtained according to the invention, and the corresponding phase image.
Figure 19:

FIGS. 18 and 19 show fingerprints obtained in the case of moist fingers. As may be seen in FIG. 18, the intensity image contains poorly contrasted zones level with moist zones. The corresponding phase and post-fusion images obtained according to the invention are shown in FIGS. 19(a) and 19(b), respectively. The phase image is of better quality than the intensity image as it contains almost no defects that could prevent identification of the print and is directly exploitable, and the post-fusion image is also of very good quality.

Figure 22:
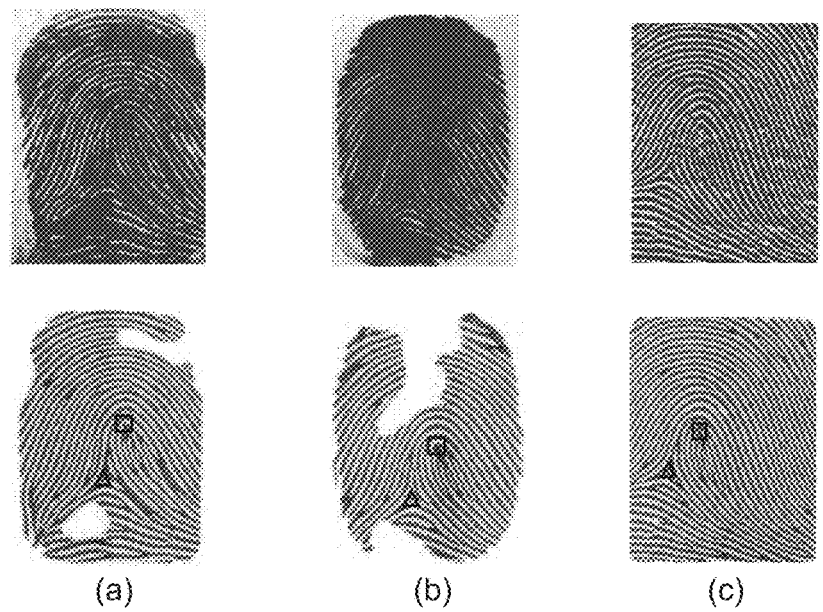
FIG. 22 illustrates a comparison of images obtained from a moist finger, with sensors according to the prior art and according to the invention.

FIGS. 22(a) and 22(b) show fingerprint images of a moist finger obtained with two known 2D sensors, an optical sensor and a capacitive sensor, respectively. Black marks due to the excessive moistness of the finger may be seen in the images. These marks considerably degrade the quality of the images, and therefore decrease authentication performance. The corresponding binarised images show that the marked zones were not recognised in the fingerprint. In comparison, the phase image obtained according to the invention, shown in FIG. 22(c), is of much better quality.

Figure 20:
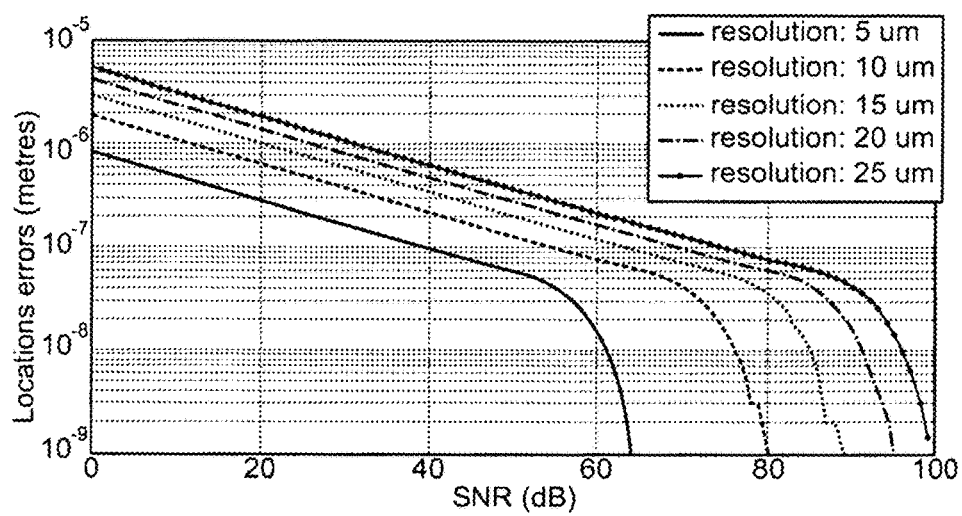
FIG. 20 is a graph showing the location error according to the invention as a function of signal-to-noise ratio and of axial resolution.

FIG. 20 shows the standard deviation of the location error as a function of signal-to-noise ratio SNR, which is defined as the ratio of the intensity level of the peak to that of the background noise (as described above with reference to FIG. 4) for various axial resolutions from 5 µm to 25 µm. For a signal-to-noise ratio of 50 dB (a typical value for backscattering at the air/skin interface) the location error is estimated to be between 60 nm and 350 nm. The location error is much lower than the axial resolution of the acquiring system, which was evaluated to be about 10 µm in the example in question. The location precision is generally much lower than the order of magnitude of the wavelength of the light source used (about equal to 1300 nm).

Assuming, according to the ergodic hypothesis, that the statistics of all of the simulated "A-scan" profiles are equivalent to spatial statistics, it would appear that the contribution of the noise during the extraction of the 3D surface of the prints is negligible with respect to the average depth of a valley (about equal to 50 µm). Thus the invention allows, via phase measurements, the bottoms and tops of the valleys of fingerprints to be correctly distinguished. Furthermore, even in the case of poorer instrument performance, i.e. for a low axial resolution, it is still possible to extract the valleys of the fingerprint with a high precision. The invention may allow OCT biometric sensors with a high imaging performance to be provided at lower cost than known sensors.

The invention is not limited to the examples just described. The identification of fingerprints in 3D requires tools that are more complex to implement than conventional 2D image mapping tools, as described in the article by A. Kumar and C. Kwong, *"Toward Contactless, Low-Cost and Accurate 3D fingerprint Identification"*, CVPR IEEE Conference, 2013, pp. 3438-3443. With the objective of making it possible to reuse tools that already exist, the 3D fingerprints obtained according to the invention are advantageously converted into 2D images by virtue of a method for mapping the texture of 3D surfaces similar to the method described in the article by G. Zigelman et al. *"Texture mapping using surface flattening via multidimensional scaling"*, IEEE transactions on Visualization and Computer Graphics, vol. 8, no. 2, 2002. This method is based on the use of the "Fast Marching" algorithm, described in the article by R. Kimmel and J. A. Sethian, *"Computing geodesic paths on manifolds"*, applied mathematics, Vol. 95, pp. 8431-8435, 1998, and the "multidimensional scaling" (MDS) algorithm. In particular, to flatten a 3D fingerprint, the "Fast Marching" algorithm is used to calculate geodesic distances from a triangular mesh of its average envelope, i.e. the 3D surface of the print without its valleys. The "multidimensional scaling" algorithm is applied to convert the mesh 3D surface into a 2D image, under the constraint of minimisation of distortions in the geodesic distances. This makes it possible to preserve as best as possible the distances between the minutiae, this being particularly advantageous in the context of biometry. Various texture images may be projected onto this flattened 2D surface, for example the intensity texture image I(x,y), the phase texture image P(x,y) or the fused texture image F(x,y). However, the invention is not limited to a particular type of method for converting the 3D images into 2D images.

Apart from the sector of biometry, the invention may be used in the morphological study and analysis of biological materials, especially in the medical field, for example for medical imaging requiring the study of the morphology of surfaces of biological materials located at depth under the skin.

The invention may be used in order to detect another fraud technique that consists in removing the external fingerprint, thereby making any authentication technique based on the external print inoperable. If it is being sought to detect a fraud, rather than to authenticate an individual, the fact that no external print is detectable even though an internal print is may lead to the triggering of an indicator of a possible fraud.

The invention claimed is:

1. A method for extracting morphological characteristics from a sample of biological material comprising an internal and an external print, using an optical coherence tomography acquiring system delivering a signal representative of the sample, the method comprising forming based at least on the signal representative of the sample an image containing intensity data and an image containing phase data corresponding to the time of flight of light in order to extract the morphological characteristics, wherein in order to form the image containing phase data corresponding to the time of flight of the light a position of a peak of interest of a profile of reflectivity of the light with depth is determined, the reflectivity profile being established from the signal delivered by the acquiring system and comprising a first peak corresponding to the external print and a second peak corresponding to the internal print, said peak of interest being chosen among first and second peaks depending on whether data to be extracted are those of the external print or of the internal print.

2. The method according to claim 1, wherein a phase image is formed using as reference an average envelope Em(x,y) of a 3D surface of the corresponding print.

3. The method according to claim 2, wherein the phase image is given by P(x,y)=S(x,y)−Em(x,y), where S(x,y) is a topographical image of the 3D surface of the corresponding print, which image is obtained from the determination of the position of the maximum reflectivity peaks for A-scans (x,y) of a tomographic volume.

4. The method according to claim 3, wherein the image containing intensity data and the phase image P(x,y) are fused to form a single image.

5. The method according to claim 2, wherein the phase image is projected onto the 3D surface of the corresponding internal print.

6. The method according to claim 1, wherein the image containing intensity data and the image containing phase data are fused to form a single image.

7. The method according to claim 6, wherein to fuse the image containing intensity data and the image containing phase data, a structure of each image is analysed in order to establish, for each image, a confidence map containing, for each pixel, a quality value depending on neighbouring pixels.

8. The method according claim 7, wherein each pixel of the image fused from the image containing intensity data and the image containing phase data is the result of a linear combination of the values of corresponding pixels of the two images, weighted by the quality values of the confidence maps.

9. The method according to claim 8, the sample being a fingerprint, the quality value of a pixel is obtained from print valley orientation field reliability maps.

10. The method according to claim 7, wherein the image fused from the image containing intensity data and the image containing phase data is formed by retaining, for each pixel, the pixel of the image having a highest quality value.

11. The method according to claim 1, wherein the position of the peak of interest is estimated and then spatial filtering is carried out on the signal, the filtering comprising retaining an interferometric signal contained in a window centered on the peak of interest and of a predefined width.

12. The method of claim 11, the predefined width being of an order of magnitude of an axial resolution of the acquiring system.

13. The method of claim 11, wherein a transformation is applied to the spatially filtered signal in order to obtain spectral data relating to a scattering recorded at an air/finger interface in the case of the external print or at an epidermal/dermal interface in the case of the internal print.

14. The method according to claim 13, wherein in order to obtain phase data to form the phase image, a slope of the phase is calculated by linear regression of the spectral dependence of the phase, which is obtained from spectral data obtained by transforming the spatially filtered signal.

15. Method for detecting fraud using overlayers, in which the method as defined in claim 1 is implemented and the fingerprint associated with the first reflectivity peak is compared with that associated with the second peak.

16. A device for extracting morphological characteristics from a sample of biological material comprising internal and external prints, comprising an optical coherence tomography acquiring system delivering a signal representative of the sample, the device being configured to form, from at least the signal delivered by the acquiring system and representative of the sample, an image containing intensity data and an image containing phase data corresponding to the time of flight of light, the device being configured, in order to form the image containing phase data corresponding to the time of flight of the light, to determine a position of a reflectivity peak of interest of a profile of reflectivity of the light with depth, said profile being established from the signal delivered by the acquiring system, the reflectivity profile comprising a first peak corresponding to the external print and a second peak corresponding to the internal print, said peak of interest being chosen among first and second peaks depending on whether data to be extracted are those of the external print or of the internal print.

17. Device according to claim 16, being configured to form a phase image P(x,y) using as reference an average envelope Em(x,y) of the 3D surface of the print, where P(x,y)=S(x,y)−Em(x,y), where S(x, y) is a topographic image of the 3D surface of the print, which image is obtained from the determination of the position of the maximum reflectivity peak of interest for each A-scan(x,y) of a tomographic volume, and to fuse the intensity image I(x,y) and the phase image P(x,y) in order to form a fused image F(x,y), and once the position of the peak of interest has been estimated, to carry out spatial filtering on the signal, the filtering consisting at least in retaining the interferometric signal contained in a window centred on the peak of interest and of a predefined width and to apply a transformation to the spatially filtered signal in order to obtain spectral data relating to the scattering recorded at an air/finger interface in the case of an external print or at the epidermal/dermal interface in the case of an internal print, and, in order to obtain the phase data required to form the phase image, to calculate the slope of the phase by linear regression of a spectral dependence of the phase, which is obtained from spectral data obtained by transforming the spatially filtered signal.

* * * * *